United States Patent [19]

Ceriani et al.

[11] Patent Number: 5,075,219
[45] Date of Patent: Dec. 24, 1991

[54] MONOCLONAL ANTIBODY WHICH RECOGNIZES A SPECIFIC GLYCOPROTEIN OF A HUMAN MILK-FAT GLOBULE MEMBRANE MUCIN ANTIGEN AND SAID MUCIN ANTIGEN

[75] Inventors: Roberto L. Ceriani; Jerry A. Peterson, both of Lafayette, Calif.

[73] Assignee: John Muir Cancer & Aging Institute, Walnut Creek, Calif.

[21] Appl. No.: 333,457

[22] Filed: Apr. 5, 1989

[51] Int. Cl.$^5$ .................. C12Q 1/00; G01N 33/53; C12N 15/00; C12N 5/00
[52] U.S. Cl. .................. 435/723; 435/172.2; 435/240.27; 436/548.1; 530/387; 935/104
[58] Field of Search .................. 435/7, 172.2, 240.26, 435/240.27; 436/503, 518, 543, 547, 548, 800, 811, 813, 819; 530/387, 389, 812, 828, 832, 836, 809; 424/3, 85.8; 935/89, 103, 104, 106, 107, 95; 485/7.1, 7.23

[56] References Cited

PUBLICATIONS

Griffiths, A. et al., Int Jour Cancer 40:319–327 (1987).
Buchell, J. et al., Jour Immunol. 131(1):508–513 (1983).
Gendler, S., et al., PNAS 84:6060–6064 (1987).
Arklie, J. et al., Biol Abstr 73(1982) #26174.
van Hell, H. et al., In "Alternative Immunoassays", (Collins, ed., Wiley & Son, Publ.) 1985, pp. 39–58.
H. M. Geysen et al., Proc. Natl. Acad. Sci., 81: 3998–4002 (1984).

*Primary Examiner*—Esther L. Kepplinger
*Assistant Examiner*—Jacintha M. Stall
*Attorney, Agent, or Firm*—Myron C. Cass

[57] ABSTRACT

A hybridoma cell line is provided which is capable of producing a monoclonal antibody which binds to a unique determinant site on the surface and in the cytoplasm of human breast carcinoma cells and cells of other adenocarcinomas and does not bind selectively to the surface of normal breast epithelial cells except in instances of high concentration of the antibody in the testing fluid. The cell line of the invention was developed by immunizing mice with a select group of immunogens and a conventional myeloma cell line for fusion with the murine splenocytes harvested. The monoclonal antibody is identified as the BrE3 monoclonal antibody. The BrE3 monoclonal antibody binds to an antigen which is characterized as a high molecular weight glycoprotein complex having a molecular weight exceeding 400,000 daltons that is bound by a disulfide to a protein of 69,000 daltons. The BrE3 monoclonal antibody is especially useful for diagnostic detection, prognostic, and possible therapeutic application in human breast cell carcinoma.

8 Claims, No Drawings

MONOCLONAL ANTIBODY WHICH RECOGNIZES A SPECIFIC GLYCOPROTEIN OF A HUMAN MILK-FAT GLOBULE MEMBRANE MUCIN ANTIGEN AND SAID MUCIN ANTIGEN

FIELD OF THE INVENTION

This invention was made with Government funding support under National Institutes of Health grant Nos. CA39932 and S07 RR05929.

This invention relates to a monoclonal antibody which binds to antigens of human carcinomas and more particularly, relates to a monoclonal antibody which binds specifically to a mucin-like glycoprotein complex of very high molecular weight on the surface and in the cytoplasm of human breast carcinoma cells and carcinoma cells of other adenocarcinomas, and does not bind selectively to the surface of normal human breast epithelial cells except in instances of high concentration of the antibody in the testing fluid.

DESCRIPTION OF THE PRIOR ART

Monoclonal antibodies have been developed that recognize a high molecular weight mucin-like glycoprotein complex present on the surface of normal human breast epithelial cells. Peterson et al., Imperial Cancer Research Fund, London, England, March 2-3 (1981); Taylor-Papadimitriou et al., Int. J. Cancer, 28:17-21 (1981); Ceriani et al., Somatic Cell Genetics, 9:415-427 (1983). Other investigators have developed monoclonal antibodies using both the human milk fat globule as the immunizing agent [Taylor-Papadimitriou et al., Int. J. Cancer, 28:17-21 (1981); Ceriani et al., Somatic Cell Genetics, 9:415-427 (1983)] and different breast tumor cells as the immunizing agents [Papsidero et al., Cancer Research, 43:1741-1747 (1983); Kufe et al., Hybridoma, 3:223-232 (1984); Frankel et al., J. Biol. Response Mod., 4:273-286 (1985); Colcher et al., Proc. Natl. Acad. Sci. USA, 78:3199-3203 (1981); Foster et al., Virchows Arch, 394:279-293 (1982); Ellis et al., Histopathology, 8:501-516 (1984); Ashall et al., Lancet, 2:1-11 (1982)] which were determined also to recognize a mucin-like glycoprotein. These monoclonal antibodies were found to recognize such mucin-like glycoproteins that vary in mass from approximately 250,000 daltons to over one million daltons, depending on the immunogen preparation. Shimizu et al., Biochem J., 233:725-730 (1986).

In biochemical studies of the large molecular weight mucin-like glycoproteins of the human milk fat globule membrane, it was suggested that these glycoproteins are complexes consisting of at least three distinct components which may represent at least three distinct molecular entities. Shimizu et al., Biochem J., 233:725-730 (1986). Thus, the mucin-like glycoproteins of the human milk fat globule membrane have been shown to be large molecular complexes which, due to their size, can be expected to have a myriad of epitopes. Monoclonal antibodies have been developed which bind to mucin-like glycoproteins of normal breast epithelial cells and malignant breast cells such as the Mc5 monoclonal antibody described in Ceriani et al., Somatic Cell Genetics, 9:415-427 (1983). Additionally, a monoclonal antibody D-274, specific to guinea pig milk fat globule membrane, was used to determine the distribution of mucin-like glycoproteins of greater than 400,000 daltons in both benign fibrocystic disease and infiltrating duct carcinoma of the human breast. Greenwalt et al., Am. J. Pathol., 118:351-359 (1985).

Antibodies which recognize non-mucin glycoprotein components of human milk fat globule of 68,000 daltons and 70,000 daltons have been described. Imam et al., Cancer Research 44:2016-2022 (1984); Heid et al., Biochem. Biophys. Acta 728:228-238 (1983); Gendler et al. in *Immunological Approaches to the Diagnosis and Therapy of Breast Cancer* (R. Ceriani, Ed.) Plenum Press, N.Y., pp. 33-40 (1987). These antigens differ slightly in amino acid composition, were obtained using different extraction procedures, and stain normal lactating breast apically. A 70,000 dalton protein also has been detected in the sera of breast cancer patients. Ceriani et al., Proc. Natl. Acad. Sci. USA 79:5420-5424 (1982).

Prior art monoclonal antibodies have been developed that will bind to normal human breast epithelial cells, to breast carcinoma cells, as well as, to some epithelial cells of other tissues. It would be highly advantageous in tumor cell identification, diagnosis, prognosis and therapy to provide a monoclonal antibody which will selectively bind to a unique epitope which is expressed on the surface and in the cytoplasm of human breast carcinoma cells and some carcinoma cells of other tissues and will not selectively bind to the surface of normal human breast epithelial cells.

SUMMARY OF THE INVENTION

A monoclonal antibody which selectively binds to a novel mucin-like glycoprotein antigen on the surface and in the cytoplasm of human breast carcinoma cells and carcinoma cells of other adenocarcinomas, and does not bind selectively to the surface of normal human breast epithelial cells except in instances of high concentration of the antibody in the testing fluid. The monoclonal antibody does not bind to normal tissue of the adrenal, brain, bladder, colon, esophagus, lymph node, myocardium, muscle, parathyroid, thyroid, ovary, mesothelia and liver.

The antigen recognized by the monoclonal antibody is termed BrE3 and is characterized as having a high molecular weight mucin-like glycoprotein which exceeds 400,000 daltons. The specificity of the BrE3 monoclonal antibody enables advantageous differentiation studies, prognostic, diagnostic and possible therapeutic applications in the evaluation and treatment of breast carcinomas.

The BrE3 monoclonal antibody was developed using normal delipidated human milk fat globule as the immunizing agent.

DESCRIPTION OF THE PREFERRED EMBODIMENT

Development of the monoclonal antibody embodying the invention utilized standard procedures generally described by Kohler and Milstein, Nature, 256:495-497 (1975). The host animal was immunized with whole delipidated human milk fat globule (HMFG) prepared as described in Ceriani et al., Proc. Natl. Acad. Sci. USA, 74:582-586 (1977). The host animals were New Zealand black (NZB) mice and after a suitable period of incubation, the murine spleen cells were harvested.

The harvested spleen cells thereafter were fused with P3-X63-Ag8.653 mouse myeloma cells using well known polyethylene glycol techniques. The screening for identifying the hybridoma or hybrid cell line which produced the monoclonal antibody of the invention was done using both a solid phase radioimmuno-plate binding assay and an ELISA using the HMFG and components of HMFG in wells of a microtiter plate as described in Ceriani et al., Somatic Cell Genetics, 9:415–427 (1983). Thereafter, the wells positive for HMFG were screened on cell lines from cervical carcinoma and colon carcinoma. A monoclonal antibody was identified which did not stain these latter carcinoma cell lines and the hybrid cell which produced that antibody was isolated. This monoclonal antibody is identified herein as anti-BrE3. The molecular weight or Mr of the antigen identified by the BrE3 monoclonal antibody was determined by Western Blot test as described by Towbin et al., Proc. Natl. Acad. Sci. USA, 76:4350–4354 (1979) and solid-phase binding assay as described by Ceriani et al., Monoclonal Antibodies and Functional Cell Lines, Plenum Press, New York, 398–402 (1984).

In the Western blot test, the HMFG was separated by a 7% polyacrylamide gel electrophoresis and then electroblotted to nitrocellulose paper. The nitrocellulose was cut into strips and the strips incubated with the monoclonal antibody. High molecular weight standards were simultaneously run on parallel lanes of the gel.

In the solid-phase binding assay, HMFG was electrophoresed on 7% polyacrylamide gel as described by Laemmli VK, Nature, 227:680 (1970). The gel lane was sliced into fractions, the slices eluted, and the eluate dried onto microtiter plates. Binding of monoclonal antibody was tested by a radioimmunobinding assay technique. When the HMFG was electrophoresed, in both the Western blot test and the solid-phase binding assay, the monoclonal antibody BrE3 identified a material found only at the origin of the polyacrylamide gel. Thus, the mucin-like glycoprotein antigen identified by the monoclonal antibody BrE3 remained at the origin and did not penetrate the polyacrylamide gel. The HMFG then was electrophoresed on less than 7% polyacrylamide gel using the solid-phase binding assay previously described. The molecular weight of the mucin-like glycoprotein antigen of HMFG identified by the monoclonal antibody BrE3 was then calculated using high molecular weight standards. The molecular weight of this antigen was estimated to exceed 400,000 daltons.

In assays of body fluids which contained breast carcinoma cells or molecules using the BrE3 monoclonal antibody, we determined that, in addition to a glycoprotein of more than 400,000 daltons, there also occurred binding to a glycoprotein molecular entity which exhibited a molecular weight of less than 400,000 daltons. It was postulated that the high molecular weight mucin-like glycoprotein antigen to which the BrE3 monoclonal antibody bound had become denatured in the body fluid such as to fragmentize. It appears the BrE3 monoclonal antibody recognizes an epitope common to the >400,000 molecular weight antigen and a smaller molecular entity or fragment which can result from the breakup of the >400,000, molecular weight species. Thus, although the BrE3 monoclonal antibody binds specifically to the high molecular weight antigen exceeding 400,000 daltons, it also can bind to a common epitope of the antigen found on such a molecular entity. This is possible since the high molecular weight antigen appears to be a complex of molecular entities.

Further study of the high or complex molecular weight antigen exceeding 400,000 daltons was undertaken. HMFG membranes, prepared as previously described, were initially solubilized in PBS containing 0.3% Triton X-100 at a concentration of 5 mg/ml. The solubilized membranes were subjected to affinity chromatography on Sepharose beads that were covalently bound to the BrE3 monoclonal antibody. The material bound to the beads was eluted with 2% sodium dodecyl sulface (SDS). The eluted material was run in 7% polyacrylamide gels in the presence of SDS with or without mercaptoethanol as a reducing agent, and transfered to a nitrocellulose sheet for Western blotting. It was possible to establish that the reduction protein released from the mucin-complex separated by affinity chromatography by the BrE3 monoclonal antibody s a 69,000 dalton antigen that was detected by McR2 [Ceriani et al., Somatic Cell Genetics, 9:415–427 (1983)] but not by BrE3 monoclonal antibody.

The anti-BrE3 monoclonal antibody co-precipitated a 69,000 dalton protein and both the 69,000 dalton protein and the mucin-like glycoprotein complex remained at the origin of the polyacrylamide gel under non-reducing conditions. Upon reduction, the 69,000 protein antigen was released and migrated as a doublet with the major band at 69,000 daltons.

The possibility that reduction merely broke apart the mucin thus releasing a physically trapped 69,000 dalton protein was studied. HMFG was dissolved in buffers containing 0.3–1.0% Triton X-100, 0.1%–2% SDS, 1% SDS plus 8M urea and 6M guanidine hydrochloride. Then, the HMFG was treated with neuraminidase and endo-N-acetylgalactosaminidase and extensively sonicated. None of these procedures released the 69,000 dalton protein from the mucin-like glycoprotein complex. Co-precipitation of BrE3 antigen with antibodycoated beads demonstrated that the 69,000 dalton band was in fact complexed with the mucin and not to another high molecular weight species. It therefore appears that the 69,000 dalton protein is covalently linked to mucin by a disulfide bond.

The BrE3 monoclonal antibody isotype was determined to be IgG1 by using a mouse immunoglobulin kit.

The BrE3 monoclonal antibody was tested extensively for binding to histological sections in order to further characterize its tissue binding specificity. Standard immunoperoxidase assay procedures were used for binding to histological sections of normal and cancerous human tissue. The tissues were prepared in the form of multi-tumor tissue blocks as described by Battifora, H., Lab Invest., 55:244.248 (1986). Each tissue block was prepared from a collection of strips of fixed tissues by wrapping the tissues in peritoneal membrane or intestine and embedding in paraffin. The blocks then were sliced in preparation for the binding studies. In this manner, a large number of different tissues were assessed with a single staining.

The breast block used to characterize the BrE3 monoclonal antibody contained 21 different specimens from normal breast tissues, 22 adenomas, and 33 breast carcinomas. The BrE3 monoclonal antibody stained all test tissues tested.

In tests conducted by immunoperoxidase staining on paraffin sections of normal human breast epithelial cells, the BrE3 monoclonal antibody was found not to bind selectively to the surface of human breast epithelial cells except under conditions of relatively high concentrations of the monoclonal antibody. Generally, the monoclonal antibody did detect secretory material present in the lumen, preferentially of ducts, of the normal breast gland. However, the BrE3 monoclonal antibody was found to bind to the surface of human breast tumor cells intensely at significantly lower concentrations of the monoclonal antibody. Such binding of the monoclonal antibody also was detected in the cytoplasm of the breast tumor cells tested. For instance, in a comparison test of normal breast epithelial cells and breast tumor cells, the required concentration of monoclonal antibody relative to the tumor cells for meaningful results was at least one tenth (1/10) of the required concentration of monoclonal antibody relative to the normal breast epithelial cells for detecting staining by the monoclonal antibody. Thus, the BrE3 monoclonal antibody can stain normal human breast cells at high concentrations of monoclonal antibody Typically, a biological sample of human carcinoma cells such as breast carcinoma cells thought to contain the BrE3 antigen, or substances derived from the carcinoma cells which substances are thought to contain the BrE3 antigen, are contacted with labelled BrE3 monoclonal antibody. The labelled antibody and antigen are contacted for a length of time and under conditions sufficient for the formation of an immunological complex between the antibody and the antigen. The immunological complex is separated from the reaction system and analyzed to determine the presence of BrE3 antigen. in the test sample, but it will stain human breast tumor cells selectively and intensely at even relatively lower concentrations of antibody in the test sample. This binding characteristic of the BrE3 monoclonal antibody was determined to apply also to the other adenocarcinomas referenced herein.

The BrE3 monoclonal antibody was tested on paraffin sections by immunoperoxidase staining of normal human breast epithelial cells. Generally the BrE3 monoclonal antibody detected secretory material present in the lumen, preferentially of ducts, of the normal breast gland. In contrast, breast tumor stained with BrE3 monoclonal antibody in many instances intensely and in most cases in the cytoplasm of the breast cancer cells. In most tumors, a concentration of BrE3 monoclonal antibody at least one tenth (1/10) of that required to stain secretary material in ducts of normal breast was enough to intensely stain breast tumor cells. The BrE3 monoclonal antibody therefore did not selectively bind to the surface of normal human breast epithelial cells except in instances of high concentration of the antibody in the testing fluid.

The BrE3 monoclonal antibody was also tested on a large panel of different normal and tumor tissues other than normal breast tissue or breast carcinoma. The BrE3 monoclonal antibody bound to normal tissues of the alveolar lining cells of the lung, the distal convoluted tubules of the kidney, the acinar epithelium cells of the pancreas and the entire thickness of the mucosa of the stomach. The BrE3 monoclonal antibody did not bind to normal tissue of the adrenal, brain, bladder, colon, esophagus, lymph node, mycocardia, muscle, parathyroid, thyroid, ovary, mesothelia and liver.

The BrE3 monoclonal antibody bound to numerous adenocarcinomas. A combination of apical membrane staining and cytoplasmic staining was noticed in the majority of adenocarcinomas. The BrE3 monoclonal antibody bound to a majority of adenocarcinomas of the breast, lung, ovary, bladder, endometrium, stomach and mesothelioma. The BrE3 monoclonal antibody bound to a lower number of adenocarcinomas of the colon, kidney, liver, lymph node, merkel cell, pancreas, parotid, rhadbosarcoma, salivary gland, sarcoma and thyroid. The BrE3 monoclonal antibody also bound to tumors of the cervix and larnyx.

A sample of the hybrid cell line capable of producing the BrE3 monoclonal antibody is on deposit with the American Type Culture Collection, 12301 Parklawn Drive, Rockville, Md., 20852 as of Feb. 7, 1989, and is assigned A.T.C.C. No. HB 10028.

The BrE3 monoclonal antibody is unique because of its exceptional specificity for a mucin-like glycoprotein complex of very high molecular weight present on the surface and in the cytoplasm of breast carcinoma cells and which expresses no specificity for normal tissue of the adrenal, brain, bladder, colon, esophagus, lymph node, myocardia, muscle, parathyroid, thyroid, mesothelia and liver. Consequently the BrE3 monoclonal antibody can be useful in several ways. It can be used as one component of a "cocktail" of anti-breast antibodies, each having different binding specificities. Since the cocktail is composed of monoclonal antibodies having different cell and tissue specificity, it is useful for breast carcinoma diagnosis and therapy, as well as. studying cell differentiation and cell-type specificity. For example, the BrE3 monoclonal antibody can be tagged with a detectable label such as a dye or fluorescent molecules or a radioactive tracer for tumor imaging. A suitable tracer would be Iodine$^{131}$, Indium$^{111}$ or Technetium$^{99}$. The BrE3 monoclonal antibody can be used therapeutically both in conjugated and unconjugated forms in a cocktail of several monoclonal antibodies or separately. Suitable conjugates for the BrE3 monoclonal antibody include chemotherapeutic drugs, toxins or radioisotopes. Radioisotopes, such as Iodine$^{131}$, can be conjugated directly to the BrE3 monoclonal antibody. Radioisotopes such as Indium$^{111}$ or Yttrium$^{90}$ can be conjugated indirectly to the BrE3 monoclonal antibody through the use of chelators or by other known means. The conjugated or unconjugated BrE3 monoclonal antibody may be administered in a cocktail of monoclonal antibodies or in separate dose form.

Examples of monoclonal antibodies which may be used in such a cocktail of monoclonal antibodies are disclosed in our co-pending U.S. patent application Ser. Nos. 153,072 and 237,218, which enjoy common ownership.

Immunoassay in which microspheres are utilized in conjunction with antigens or antibodies coated thereon and suitably tagged or labelled, can be employed for in vitro diagnostic applications with the BrE3 monoclonal antibody. The labels or tags may be varied as discussed herein and known in the art. For in vitro applications, the BrE3 monoclonal antibody may be provided in an assay kit accompanied by other ingredients for completing the assay of a biological sample according to assay instructions in insert literature, for instance. The same may be feasible for in vivo applications, both for diagnostic and therapeutic uses. The assay may be used with flow cytometric procedures to study cell differentiation and cell specificity. The BrE3 monoclonal antibody also may be used as a prognostic tool in the histopathology of tumors to determine, for example, the outcome of a malignancy, the likelihood of dissemination of a malignancy or the stage of the malignancy. These examples of in vitro and in vivo applications should not be deemed to exclude other applications of the use of the BrE3 monoclonal antibody.

We claim:

1. A cell line developed by hybridoma technique which produces a monoclonal antibody specific to a unique antigenic determinant present on the surface and in the cytoplasm of human breast carcinoma cells and cells of other adenocarcinomas, said determinant being expressed on a glycoprotein molecular complex of molecular weight exceeding 400,000 daltons, said cell line being on deposit with the A.T.C.C., Deposit No. 10028.

2. The cell line according to claim 1 wherein said monoclonal antibody producing cells are hybridoma cells produced from mouse spleen cells immunized with delipidated human milk fat globule.

3. The cell line according to claim 1 in which said monoclonal antibody producing cells are hybridoma cells produced from mouse spleen cells immunized with normal whole human milk fat globule membrane.

4. The cell line according to claim 1 in which said monoclonal antibody producing cells are hybridoma cells produced from mouse spleen cells immunized with normal human milk fat globule components.

5. The cell line according to claim 1 in which said monoclonal antibody has no binding specificity to normal epithelial cells selected from the group consisting of the adrenal, brain, bladder, colon, esophagus, lymph node, myocardia, muscle, parathyroid, thyroid, ovary, mesothelia and liver.

6. The cell line according to claim 1 in which said monoclonal antibody specifically binds to normal epithelial cells selected from the group consisting of the alveolar lining cells of the lung, the distal convoluted tubules of the kidney, the acinar epithelium of the pancreas, and the mucosa of the stomach.

7. The cell line according to claim 1 in which said monoclonal antibody specifically binds to epithelial cells of adenocarcinomas selected from the group consisting of adenocarcinomas of the breast, lung, ovary, bladder, endometrium, stomach and mesothelioma.

8. A monoclonal antibody produced by the hybridoma cell line sample on deposit with the American Type Culture Collection and assigned A.T.C.C. deposit No. 10028.

* * * * *

UNITED STATES PATENT AND TRADEMARK OFFICE
CERTIFICATE OF CORRECTION

PATENT NO. : 5,075,219

DATED : December 24, 1991

INVENTOR(S) : Roberto L. Ceriani and Jerry A. Peterson

It is certified that error appears in the above-identified patent and that said Letters Patent is hereby corrected as shown below:

TITLE PAGE:

Abstract, line 17, after "disulfide" insert --bond--.

Column 3, line 47, after "addition" insert
    --to binding--.

Column 3, line 61, cancel "daltons." and insert
    --daltons,--.

Column 4, line 13, cancel "s" and insert --as--.

Column 5, lines 11-13, cancel "Thus, the BrE3 monoclonal antibody can stain normal human breast cells at high concentrations of monoclonal antibody".

Column 5, line 24, after "antigen." insert --Thus, the BrE3 monoclonal antibody can stain normal human breast cells at high concentrations of monoclonal antibody--.

Column 6, line 21, cancel "as." and insert --as,--.

Signed and Sealed this

Twenty-second Day of September, 1992

*Attest:*

DOUGLAS B. COMER

*Attesting Officer*      *Acting Commissioner of Patents and Trademarks*